United States Patent
Gochar, Jr.

(10) Patent No.: US 6,784,447 B2
(45) Date of Patent: Aug. 31, 2004

(54) VISION SYSTEM WITH REFLECTIVE DEVICE FOR INDUSTRIAL PARTS

(75) Inventor: Joseph P. Gochar, Jr., Catonsville, MD (US)

(73) Assignee: Logical Systems, Inc., Baltimore, MD (US)

( * ) Notice: Subject to any disclaimer, the term of this patent is extended or adjusted under 35 U.S.C. 154(b) by 275 days.

(21) Appl. No.: 10/139,718

(22) Filed: May 6, 2002

(65) Prior Publication Data

US 2002/0125450 A1 Sep. 12, 2002

Related U.S. Application Data

(63) Continuation-in-part of application No. 09/411,674, filed on Oct. 7, 1999, now Pat. No. 6,384,421.

(51) Int. Cl.⁷ .............................................. G01N 21/86
(52) U.S. Cl. .............................. 250/559.46; 250/223 R; 356/238.1
(58) Field of Search ........................ 250/208.1, 223 R, 250/223 B, 559.05, 559.07, 559.08, 559.46; 356/238.1, 428, 430; 700/127; 702/40; 209/524, 526, 536, 538, 548, 563, 576, 577, 587, 588, 651, 655, 701, 939; 438/125, 127, 128, 131, 132

(56) References Cited

U.S. PATENT DOCUMENTS

| | | |
|---|---|---|
| 4,196,811 A | 4/1980 | Pilesi et al. |
| 4,308,959 A | 1/1982 | Hoover et al. |
| 4,394,683 A | 7/1983 | Liptay-Wagner et al. |
| 4,709,800 A | 12/1987 | Olsen |
| 4,882,498 A | 11/1989 | Cochran et al. |
| 4,915,237 A | 4/1990 | Chang et al. |
| 4,924,107 A | 5/1990 | Tucker |
| 4,946,025 A | 8/1990 | Murphy |
| 4,972,093 A | 11/1990 | Cochran |
| 5,051,825 A | 9/1991 | Cochran et al. |
| 5,068,799 A | 11/1991 | Jarrett, Jr. |
| 5,072,127 A | 12/1991 | Cochran et al. |

(List continued on next page.)

FOREIGN PATENT DOCUMENTS

| | | |
|---|---|---|
| GB | 2005826 | 4/1979 |
| GB | 2066455 | 7/1981 |
| GB | 2078948 | 1/1982 |
| GB | 2136954 | 9/1984 |
| JP | 11108853 | 4/1999 |
| WO | EP0572336 | 12/1993 |

OTHER PUBLICATIONS

*British Search Report*, May 16, 2001; 1 pg.
IC Vision, *Inspector Product Literature*, Feb. 22, 2001; 16 pgs.
Kirin Techno–System Corp., *Cap Inspection System for PET Bottles with Mirror Box*, Web Site Printout, pp. 1–4, Dec. 16, 2003.

Primary Examiner—Stephone B. Allen
(74) Attorney, Agent, or Firm—Wood, Herron & Evans, LLP

(57) ABSTRACT

A machine vision inspection system for industrial parts such as plastic molded caps or the like can reliably detect defects at very high inspection rates on the order of 1600 per minute of a variety of cap colors and liners including previously difficult to inspect combinations. Advantageously, the system includes an inclined inspection ramp which provides separation between the caps which are processed through an inspection station to provide accurate imaging of each individual cap without interference from adjacent caps. Further, the inspection station includes a reflective device which provides accurate and reliable imaging of numerous views of caps with a single color to detect and identify defects.

28 Claims, 3 Drawing Sheets

U.S. PATENT DOCUMENTS

| | | |
|---|---|---|
| 5,074,397 A | 12/1991 | Mukai et al. |
| 5,095,290 A | 3/1992 | Sevenhans et al. |
| 5,172,005 A | 12/1992 | Cochran et al. |
| 5,303,811 A | 4/1994 | Haley |
| 5,331,151 A | 7/1994 | Cochran et al. |
| 5,353,909 A | 10/1994 | Mukai et al. |
| 5,365,084 A | 11/1994 | Cochran et al. |
| 5,404,227 A | 4/1995 | Sumita et al. |
| 5,440,385 A | 8/1995 | Fein et al. |
| 5,444,480 A | 8/1995 | Sumita |
| 5,451,773 A | 9/1995 | Triner et al. |
| 5,572,433 A | 11/1996 | Falconer et al. |
| 5,581,074 A | 12/1996 | Yoshida |
| 5,591,462 A | 1/1997 | Darling et al. |
| 5,592,286 A | 1/1997 | Fedor |
| 5,695,302 A | 12/1997 | Hilbish |
| 5,699,152 A | 12/1997 | Fedor et al. |
| 5,745,593 A | 4/1998 | Wahawisan et al. |
| 5,805,279 A | 9/1998 | Palombo et al. |
| 5,880,359 A | 3/1999 | Kono et al. |
| 5,911,003 A | 6/1999 | Sones |
| 5,936,353 A | 8/1999 | Triner et al. |
| 6,296,102 B1 | 10/2001 | Uchida et al. |
| 6,304,323 B1 | 10/2001 | Ishikura et al. |
| 6,661,911 B1 | 12/2003 | Ishikura et al. |

VISION SYSTEM WITH REFLECTIVE DEVICE FOR INDUSTRIAL PARTS

This is a continuation-in-part of U.S. patent application Ser. No. 09/411,674, filed Oct. 7, 1999, issued as U.S. Pat. No. 6,384,421 on May 7, 2002 and hereby incorporated by reference in its entirety.

BACKGROUND OF THE INVENTION

This invention relates to article inspection systems and, particularly, to vision systems for inspecting work pieces such as plastic molded closure caps for containers and the like.

During the manufacture of many parts such as plastic molded closure caps, a number of defects in the closure cap may exist which should cause the cap to be rejected. Commonly, closure caps of this type have a liner inserted therein against the inner surface of an end wall of the cap. Typically, the cap has a skirt projecting annularly from the peripheral rim of the end wall and the skirt may include a closure or sealing mechanism such as threads for cooperation with mating threads around the neck of a bottle, container or the like. Examples of defects in such closure caps include a liner which is positioned off center within the closure, a missing liner, a malformed liner (commonly referred to as a "moon-cut" liner), a cap which is asymmetric or off-round, a cap having an edge broken or flashing on the edge from extraneous plastic material, a pull tab defect on the liner or other similar problems. Such flaws or defects are sometimes produced during the manufacturing process and/or as a result of contamination or damage after manufacture, but prior to the filling of the container.

Machine vision systems represent one technology for acquiring or sensing an image of at least a selected portion of a work piece, such as a cap as previously described, through an electronic sensor or camera. The image generated by the camera is then analyzed by a computer program for one or more of the above-described defects. Vision systems are commonly used to determine the existence of any marks or defects in the image of the cap and the acceptability of any such marks or defects by use of a vision computer as described.

While human vision may out perform its automatic equivalent in the ability to analyze very complex, everyday scenes, when it comes to repeated tasks, such as the inspection of plastic molded caps over and over again, a human observer understandably tires, loses concentration and makes mistakes. Machine vision inspection of such articles is known to provide some important advantages, including sophisticated image processing/analysis, repeatable performance, image acquisition for diagnosis and set up, ability to inspect a variety of articles in large tolerance and required part placement. Moreover, at inspection rates of up to 1600 parts per minute or more, each part or cap spends on the order of 33 milliseconds at an inspection station. At such speeds, only a machine vision system is fast enough to reliably and repeatedly inspect such articles.

While known vision systems have the above-described advantages for inspecting articles such as plastic molded caps and the like, they do have specific and significant limitations. Vision systems typically rely on television or video cameras to image the article to be inspected and detect any flaws. The resolution of the camera, or its ability to detect a flaw, is directly related to its ability to capture an accurate and reliable image of each individual cap, article or similar item. Typically, plastic molded caps, for example, are manufactured by the tens of thousands and each individual cap must be inspected by the vision system for quality control purposes. The large volume of caps are typically gathered in an accumulated mass and, at best, are similarly oriented on a flat surface. For accurate vision inspection and detection of flaws, the vision system must be able to precisely and accurately produce an image of each individual cap without interference from the surrounding environment or other caps.

Furthermore, inspection rates required of such systems mandate that the individual images be serially produced, analyzed and acted upon accordingly for each individual cap, once again without interference, for accurate detection of relatively small flaws or problems.

Additionally, plastic molded caps, like most objects being inspected by vision systems, are three-dimensional and have a variety of features and geometries that must be captured by the vision system for analysis. Because of the limited field of view of standard cameras and known vision systems, typically multiple cameras oriented at different angles and having differing fields of view of the work piece or plastic molded cap are utilized to obtain the required information for proper analysis. Utilizing multiple cameras to obtain the required views and information for analysis is both expensive from a hardware equipment standpoint as well as complex and cumbersome from an analysis and vision systems software perspective. For example, one type of plastic molded cap includes a liner having a tab which is folded under between the liner and the adjacent end wall of the cap. Ultimately, the liner is intended to be adhered to the upper rim on the mouth of the container so that when the consumer initially opens the container by unscrewing the cap, the liner remains on the mouth of the cap. The user then would lift the liner from the container by pulling on the now exposed tab. However, during the manufacture of the cap and liner combination, occasionally, the tab is not properly folded under between the end wall and the liner and is presented as a standing tab projecting upwardly from the liner typically along the threaded region of the skirt of the cap. Alternatively, the tab may be missing entirely from the liner.

Other possible defects with plastic molded caps of this type include excess glue or foreign matter on the threads of the skirt of the cap, the top edge of the skirt when the cap is inverted may be malformed from a "short shot" during the injection molding process or other similar defects which must be identified by a vision system. Such defects are difficult if not impossible to accurately assess in a timely and efficient manner with a standard single camera system due to the orientation, geometry, and three-dimensional configuration of the plastic molded cap and liner combination.

SUMMARY OF THE INVENTION

This invention provides a machine vision inspection system for inspecting work pieces such as caps and other articles and an associated method for doing so which overcomes the above-stated and other limitations with known systems/methods.

In a presently preferred embodiment, this invention is an inspection system for inspecting each of a series of serially fed work pieces in a stream of work pieces, such as plastic molded caps or the like. The system includes a feed conveyor to serially feed the caps or work pieces, each of which is typically in contact with adjacent work pieces on the feed conveyor in an accumulated mass or the like. The feed conveyor advances the caps to an inspection ramp or platform which in a presently preferred embodiment is inclined between 35° and 50°, and most preferably at 40° with respect to a horizontal plane. The inspection ramp has a reduced friction upper surface upon which the caps or other articles advance downwardly from a top end of the inspection ramp toward a bottom end. An optional discharge conveyor is located at the bottom end of the inspection ramp to receive and discharge each of the caps for collection, packaging and/or further processing.

Advantageously, the inspection ramp is inclined so that as the caps which are in contact with one another and therefore difficult for a vision system to accurately inspect and discriminate at a top end of the ramp advance by gravity along the reduced friction surface through an inspection station located between the top and bottom ends of the ramp. The incline of the ramp produces a separation distance between each of the caps so that each cap can be individually and accurately inspected at the inspection station for defects or the like. Preferably, a pair of spaced guide rails are positioned on the lateral sides of the caps to provide for accurate lateral positioning of the caps with respect to the inspection station on the ramp.

The inspection station in a presently preferred embodiment includes an inspection window in the ramp, an infrared or other color LED strobe light source and a camera. The light source is preferably located on a back side of the inspection ramp to project light through the inspection window to back-light and illuminate each of the caps as they pass above the window. Back-lighting of the caps avoids the glare commonly generated from foil caps and liners and likewise offers a contrasting image even with white caps and white liners for accurate imaging. The inspection window and light source are preferably aligned with the camera which is located on a top side of the inspection ramp and oriented generally perpendicularly with respect to the inspection ramp at the inspection station. Preferably, the positioning of the light source, inspection window and camera provides for a full and complete image of the cap for accurate resolution and detection of possible defects in the cap.

One advantageous aspect of this invention is the ability for the inspection system to accurately and efficiently capture an image of a three-dimensional object such as a plastic molded cap while utilizing fewer and in most cases, only a single camera. Accurate images of various three-dimensional aspects of the work piece, such as an internal thread region on the skirt of the inverted cap passing on the inspection platform past the camera are accurately imaged by a single camera through the use of a reflective device which, in one embodiment of this invention is a cone. The cone is positioned within a viewing cylinder in the field of view of the camera to deflect a portion of the image of the cap, such as the thread region on the inner surface of the skirt of the cap, for accurate imaging by the camera. Additionally, portions of the field of view of the camera are not reflected by the cone so that additional aspects of the work piece can likewise by imaged and assessed by the vision system.

The system also includes a processing unit such as a computer or the like operably coupled to the camera to analyze the images of the caps generated by the camera with respect to predetermined quality control standards. For example, specific defects as described herein above, if detected by the camera, are outside of the predetermined quality control standards utilized by the computer to analyze each of the images generated by the camera. If a particular cap fails the analysis, a rejection mechanism, typically an air jet or the like, is coupled to the processing unit to receive a control signal from the processing unit and, if such a signal is received by the air jet or other rejection mechanism, the identified cap is then removed from the stream by the air jet or other rejection mechanism. The rejected cap is then discarded, analyzed or recycled as is appropriate.

This invention in a presently preferred embodiment overcomes the above-described disadvantages of known vision inspection systems by accurately and reliably providing a separation distance between each of the serially fed work pieces, articles, caps or the like to be inspected as a result of the inspection ramp and the inclination thereof. Further, the processing or inspection rate is not diminished as a result of the orientation and configuration of the inspection ramp, reflective cone and inspection station components thereby providing inspection rates as high as 1600 per minute or more depending upon the size of the items being inspected and other operational requirements.

Furthermore, heretofore difficult to inspect or analyze work pieces such as the intricate geometries of plastic molded caps and liners are reliably and effectively illuminated for accurate imaging and detection by a single camera and associated processing unit because of the opportunity for back lighting the cap with an infrared or other color LED strobe light source in combination with the reflective cone.

BRIEF DESCRIPTION OF THE DRAWINGS

The objectives and features of the invention will become more readily apparent from the following detailed description taken in conjunction with the accompanying drawings in which.

DETAILED DESCRIPTION OF THE INVENTION

Figure 1:
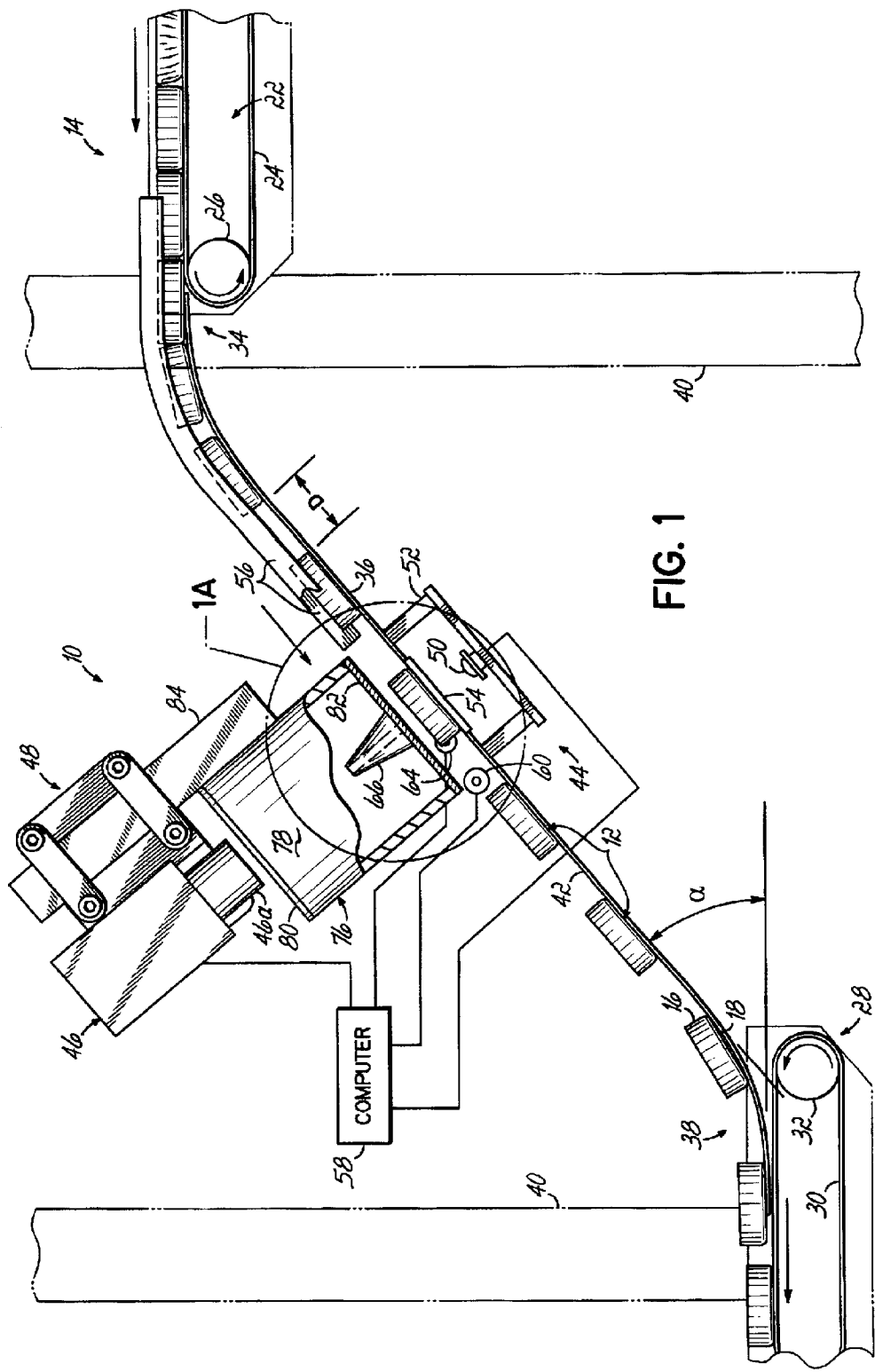
FIG. 1 is a schematic representation of a presently preferred embodiment of the vision inspection system according to this invention.

Referring to FIG. 1, a presently preferred embodiment of a vision inspection system 10 and associated method for industrial parts 12 is shown. The system 10 in a presently preferred form is utilized to inspect each of a series of serially fed work pieces in a stream of work pieces for defects or the like. The work pieces or industrial parts 12 may be any one of a variety of items such as plastic molded caps as shown in FIG. 1. Commonly, the caps 12 are produced in an injection molding or similar process (not shown) and discharged in a batch 14 or large quantities to the system 10. The caps include a peripheral skirt 16 projecting from a base or end wall 18 and a liner 20 may be inserted into the cap 12. Threads 17 are provided on the skirt 16. Preferably, the caps 12 are inverted for inspection with the skirt 16 projecting upwardly from the end wall 18. Typically, the caps 12 each include a liner 20 juxtaposed to the end wall 18 with a tab 15.

As shown in FIG. 1, the vision system 10 includes a feed conveyor 22 having a belt 24 trained for travel around a pair of rotating rollers 26 (only one of which is shown in FIG. 1), at least one of which is driven to provide rotation for the feed conveyor 22. Similarly, a discharge conveyor 28 is provided with a belt 30 trained around a pair of rollers 32 (only one of which is shown in FIG. 1), at least one of which is driven. As shown in FIG. 1, a batch 14 of caps 12 is preferably delivered to a top end 34 of an inclined inspection ramp 36 by the feed conveyor 22. Similarly, the caps 12 are discharged at a bottom end of the inspection ramp 36 onto the discharge conveyor 28 for subsequent processing, packaging or the like. Alternatively, the inspection ramp or platform 36 may be of any configuration and/or orientation, including generally horizontal in one embodiment of this invention. Commonly, the work pieces or caps 12 are accumulated together in the batch 14 or the like on the feed conveyor 22 at the top end 34 of the inspection ramp 36 such that each cap 12 is inverted and in very close proximity to, if not in touch or contact with, adjacent caps 12 as shown in FIG. 1. The inspection ramp 36 and conveyors 22, 28 are supported by appropriate support posts 40 and other structure as will be necessary for the particular arrangement, configuration and environment required for the vision system 10 as is readily understood by one of ordinary skill in the art.

The delivery rate or speed of the feed conveyor 22 depends upon the required inspection rate for the caps 12, the size of the caps 12 and other relevant factors. For example, if the caps 12 being inspected have a diameter of 1.1 inches and an inspection rate of 1600 per minute is required, the feed conveyor 22 will operate at about 1763 inches per minute maximum speed for delivery of the caps 12 to the top end 34 of the inspection ramp 36. Preferably, the inspection ramp 36 is inclined at angle α between 35° and 50° with respect to a horizontal plane and, most preferably, approximately 40° in a presently preferred embodiment. The inspection ramp 36 has an upper surface 42 upon which the caps 12 slide by gravity from the top end 34 toward the bottom end 38 thereof. The upper surface 42 of the ramp 36 is preferably a reduced friction surface and may be constructed of polished stainless steel or include a coated Teflon layer or the like. Alternatively, the ramp 36 may be constructed from UMW polyethylene and/or be made of a clear or translucent material to allow the transmission of light there through as will be described later herein.

Moreover, the top end 34 of the ramp 36 is curved as to avoid separation of the caps 12 from the upper surface 42 of the ramp 36 as the caps 12 move thereon. The shape of the top end 34 is most preferably a parabola, but may be arcuate or a chord of a circle with a five inch or more radius to maintain cap 12 contact therewith.

Positioned intermediate the top end 34 and bottom end 38 of the inspection ramp 36 is an inspection station 44 which includes a camera 46 mounted preferably generally perpendicularly with respect to the surface 42 of the ramp 36 on an upper side thereof. In a presently preferred embodiment, the camera 46 is a CCD progressive scan type camera which is readily available from many sources, including JAI (www.JAI.com) as model number CVM10BX. Appropriate support posts and mounting brackets 48 are preferably provided for the camera 46 for adjustably positioning the camera 46 both orthogonally and parallel to the ramp 36.

The inspection station 44 also includes a light source 50 preferably mounted on a support frame 52 on a back surface of the inspection ramp 36 and in-line with the viewing axis of the camera 46 to back light the cap 12 to produce an image of the cap 12 by the camera 46. In a presently preferred embodiment, the light source 50 is an infrared or other color LED strobe light which is preferably adjustable to provide a frequency as is appropriate for the inspection rate of the caps 12, typically as high as 1600 per minute depending on the size of the caps being inspected and other system 10 requirements. Some CCD cameras include an infrared cut filter installed by the manufacturer. If such is the case and an IR light source is used with this system, this filter must be removed. The light source 50 is most preferably in line with the camera 46 and on the opposite side of the cap 12 at the inspection station. However, the light source 50 may be alternatively positioned while providing back light to the cap 12 for the camera 46 within the scope of this invention. Alternatively, the light source 50 may be provided proximate the upper surface 42 of the ramp 36 for top lighting of the caps 12 in addition to or as a substitute for the back light source as shown in FIG. 1.

An inspection window 54 which is preferably transparent, translucent or the like so that at least some light may pass there through to illuminate the cap 12 may be provided at the inspection station 44 in line with the camera 46 and the light source 50 if the inspection ramp 36 is not made of a translucent, transparent or similar material. The inspection window 54 preferably produces a high diffusion of the light and may be opal glass. Alternatively, the inspection window 54 and ramp 36 may be UMW plastic with the ramp being 0.5 inches thick and the window 0.0625 inch thick for better light transmission.

The spacing of the light source 50 from the cap 12 being inspected at the inspection station 44 and the spacing of the camera 46 from the cap 12 is dependent upon the diameter of the cap and the size of the lens being utilized within the camera 46. Preferably, the spacing is optimized to fully illuminate the cap 12 while providing a full size image of the cap 12 in the field of view of the camera 46.

As the caps 12 are delivered to the top end 34 of the ramp 36, a separation distance D between the adjacent caps is created by guiding the caps 12 onto the ramp 36 that is inclined preferably at 40°. The shape of the ramp 36 and the velocity that the caps 12 are loaded onto the ramp 36 helps to ensure that the caps 12 remain in contact with the ramp 36 as they advance downwardly. Maintaining contact with the ramp 36 is an important aspect of this invention since the caps 12 must be perpendicular to the center line of the camera 46 when the image is taken for inspection purposes. The caps 12 accelerate down the ramp 36 due to gravity and the reduced friction surface 42 thereby generating the distance or spacing D between the adjacent caps 12. Separation between the caps 12 being inspected is important to provide an accurate image and subsequent analysis of each individual cap 12 without interference from the adjacent caps. Preferably, a pair of spaced guides 56 are provided at least on the upper portion of the inspection ramp 36 to maintain accurate lateral positioning between the guides 56 for the caps 12 traveling down the ramp 36 so that the caps 12 can be accurately positioned at the inspection station 44 for proper imaging by the camera 46.

Backlighting of the caps 12 by the light source 50 in many instances allows for better contrast and image quality by the vision system 10. An infrared light source 50 provides increased imaging capabilities for particular colors of caps 12, for example white caps with white liners, which with previously known vision systems are difficult to accurately inspect.

The image produced by the camera 46 of each individual cap 12 is conveyed to a computer 58 or a processing unit electrically and operably coupled to the camera 46. As with known vision systems, the processing unit or computer 58 analyzes each of the images generated by the camera 46 with respect to predetermined quality control standards to detect possible defects or problems with each cap 12, such as an upstanding tab, off-center or missing liner, a moon-cut liner, a cap which is not properly formed or similar defects. Preferably, a trigger 64 in the form of a photo-electric eye or the like is operably coupled to the computer 58 and camera 46 to detect the leading edge of the cap 12 when it is positioned on the inspection window 54. When the cap 12 is detected by the trigger 64, a signal is sent to the camera 46 and light 50 to take a picture or image of the cap 12 for inspection and analysis by the computer 58. Preferably, a vision inspection software package such as Sherlock™ (version 6.1) available from Coreco Imaging (www.coreco.com) or another suitable package is used by the computer 58 in the system 10.

If the computer 58 determines that the cap 12 has any one of a number of identifiable defects, a control signal is sent from the computer or processing unit 58 to a rejection mechanism 60 coupled thereto. The rejection mechanism 60 may be an air jet or any one of a number of items designed to remove the identified cap 12 from a stream of caps. For example, the rejection mechanism 60 is preferably a high speed rotary actuator commercially available from Ledex & Dormeyer Products (www.ledex.com). The rejection mechanism may be positioned as shown in FIG. 1 or at another position downstream from the inspection station 44 so as to produce upon receipt of the appropriate control signal a puff of air to force the cap 12 off of the ramp 36 and out of the stream for further inspection, discharge, recycling or the like. As such, when the processing unit 58 is unable to identify a defect in the cap 12, the cap 12 proceeds to the bottom end 38 of the inspection ramp 36 and onto the discharge conveyor 28 for further processing, packaging or the like.

Figure 1A:
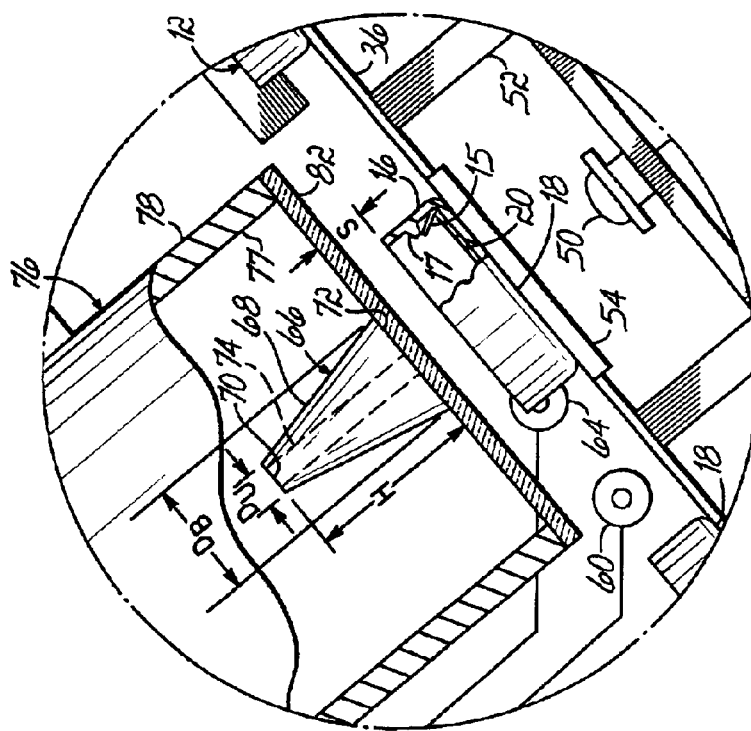
FIG. 1A is an enlarged view of the encircled portion 1A of the system of FIG. 1.

Referring to FIGS. 1 and 1A, another advantageous aspect of this invention is a reflective device 66 positioned within the field of view of the camera 46 to generate images or portions of the plastic molded cap or work piece 12 such as the threads 17 on the inner surface of the skirt 16 to produce views which would not normally be available from a single camera vision system. While the system 10 is shown and described with only one camera 46, multiple cameras could be employed within the scope of this invention. Nevertheless, the reflective device 66 affords the opportunity to use fewer, and preferably only one, camera(s) for proper imaging and analysis.

Preferably, the reflective device 66 is nonplanar; more preferably, the reflective device 66 is arcuate; and most preferably, the reflective device 66 is a truncated cone as shown in FIGS. 1 and 1A. The cone 66 has an outer side wall 68 extending between an upper end 70 and a lower base 72. The cone 66 as shown in FIGS. 1 and 1A is a truncated cone and includes a central bore 74 through the longitudinal axis, although the central bore 74 is a result of manufacturing processes used for the cone 66 and may be omitted in other embodiments. The size of the cone 66 is dependent upon the size of the work pieces or caps 12 as well as other parameters of the inspection process. The design of the reflective cone 66 is dependent upon several factors with the primary objective being in this particular application an enhanced view of the thread region 17 on the skirt 16 of the cap 12. For example, with a 38 mm cap, which typically refers to the size of the spout or opening of the container or bottle on which the cap 12 will be utilized, the height of the threads 17 on the skirt 16 of the cap 12 is typically 0.4". In this particular application, the total height H of the cone is 1.315", the diameter $D_B$ of the base 72 of the cone is 0.871", and the diameter $D_U$ of the upper end of the cone is 0.727".

The side wall 68 of the cone forms an angle of 25.66° with respect to the longitudinal axis of the cone. In one presently preferred embodiment, the cone 66 is aluminum and the side wall 68 reflective surface of the cone 66 has an optical surface which is nickel-plated at a depth of approximately 0.003" and polished to a surface accuracy of ½λ. Alternatively, a polished glass cone which is then aluminized as a mirror could be employed. The spacing S from the base 72 of the cone 66 to the upper edge of the work piece 12 such as the terminal lip on the skirt 16 of the cap is approximately 0.422". The distance $D_I$ from the cap at the inspection platform 44 or ramp 36 to the lens 46a of the camera is approximately 5.125".

The cone 66 is mounted in a viewing cylinder 76 as shown in FIGS. 1 and 1A. The viewing cylinder 76 includes a generally circular tube 78 having an inside diameter of approximately 3.00" and a height of 5.00" and is preferably PVC plastic. The interior surface 77 of the tube 78 is preferably coated or painted with a flat black finish to minimize light reflection and transmission there through. Opposite ends of the tube 78 are capped by viewing cylinder covers 80, 82 which must be transparent or nearly so to permit the transmission of the image of the work piece 12 to the camera 46. The viewing cylinder covers 80, 82 in one presently preferred embodiment are Part Nos. 8477K19, available from McMaster-Carr (www.mcmaster.com). The viewing cylinder covers 80, 82 are secured to the tube 78 using a silicone glue and the base 72 of the reflective cone 66 is attached to the lower cover 82 using Norland Optic Adhesive No. 68 with UV curing (www.norlandprod.com).

The viewing cylinder 76 and reflective cone 66 are mounted to the mounting brackets 48 on a tube 84 and secured thereto by appropriate set screws or other mechanical fasteners (not shown). Preferably, the tube 84 is coupled to the mounting bracket 48 to provide for adjustment so that the distance $D_C$ from the camera lens 46a to the reflective cone 66 and the spacing from the reflective cone 66 to the cap 12 is adjustable according to the desired application and to provide appropriate imaging for the inspection system 10. Moreover, preferably, the mounting bracket 48 provides an adjustable position toward and away from the inspection platform 36 for this purpose. The viewing cylinder 76 provides the advantages of keeping the reflective device 66 contaminant-free and clean, providing a rigid mounting to the cone 66 for proper alignment in the field of view of the camera 46 and limiting ambient light in the viewing area.

Figure 2:
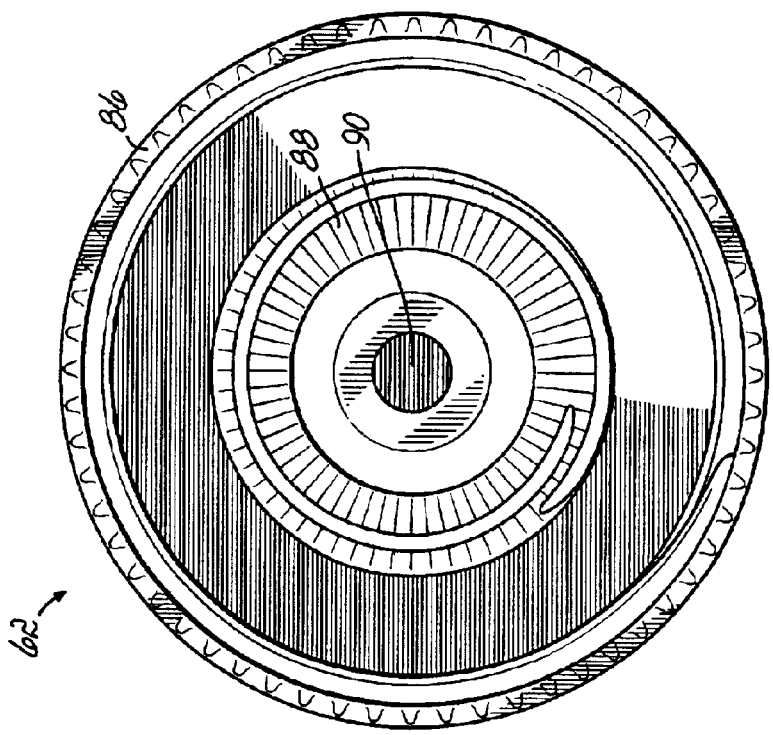
FIG. 2 is a schematic representation of an image of a plastic molded cap produced by the system.

Referring to FIG. 2, a schematic representation of an image 62 of a cap 12 and liner 20 produced according to the system 10 of FIG. 1 is shown. The image 62 was produced from an IR LED light source 50 of a 38 mm cap 12 with the liner 20.

As shown in FIG. 2, an exemplary schematic representation of image 62 of the cap 12, threads and liner 20 produced by the system 10 is shown. As a result of the reflective device 66 in the field of view of the camera 46, the image 62 includes a number of regions. For example, the direct field of view of the camera on the outer regions of the cap 12 produces a first outermost region 86 of the skirt 16 and outer perimeter of the end wall 18 and liner 20. Adjacent to the first region 68 is a reflected image 88 from the cone 66 showing a different view of the threads 17 on the skirt 16 of the cap 12. With such a view of the region 88, appropriate analysis by the vision inspection system and software affords proper analysis of the threads 17 which would not otherwise be available with a single camera 46 and without the reflective device 66. The central portion 90 of the image is the field of view of the camera 46 directly through the central bore 74 of the reflective cone 66 to the liner 20.

Figure 3:
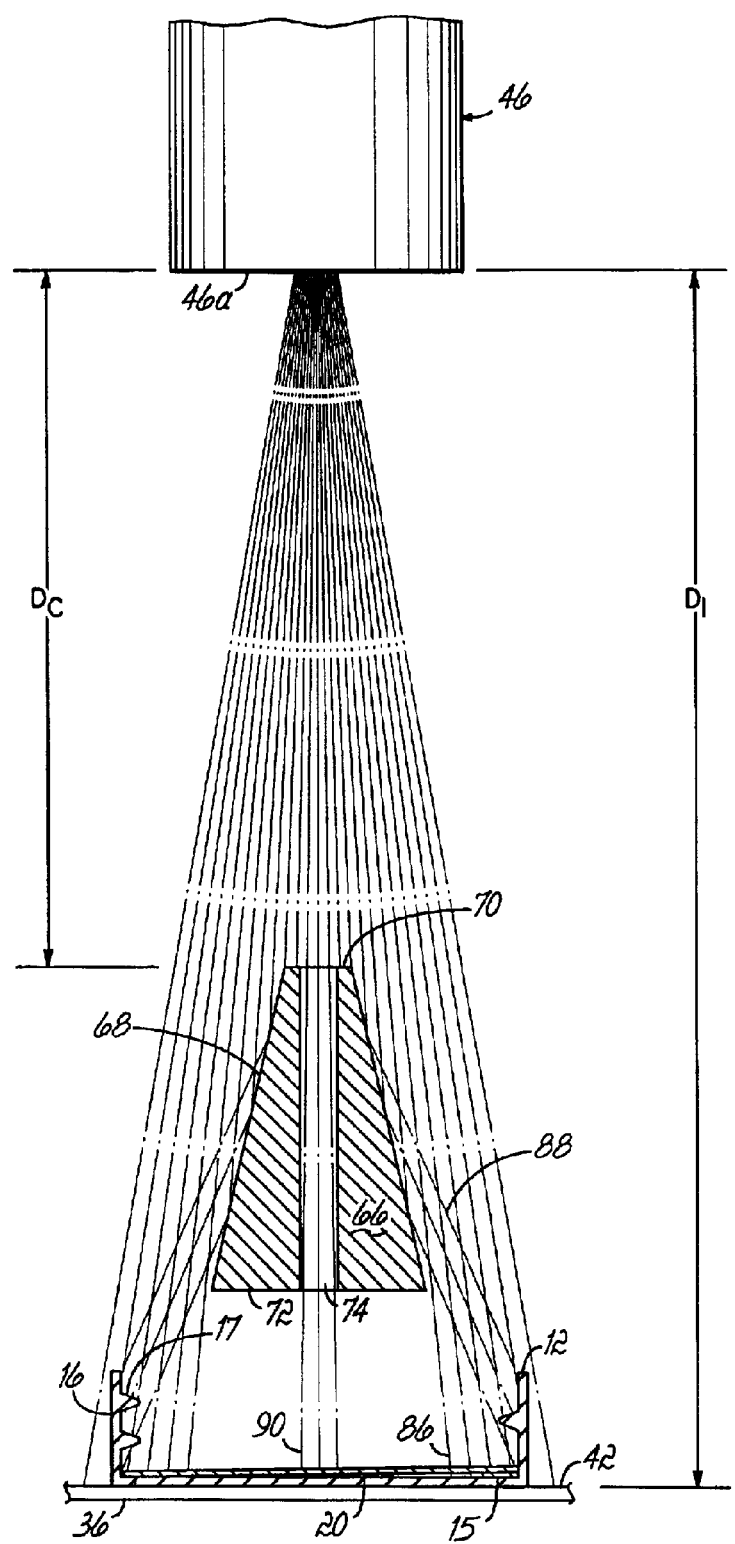
FIG. 3 is a side elevational, cross-sectional schematic representation of a camera of this system imaging the cap of FIG. 2.

The light rays shown in FIG. 3 are labeled with the reference numeral of the corresponding portion of the image 62.

It must be understood that the image 62 of FIG. 2 is exemplary only and the system 10 can be employed to produce a wide variety of other images as desired.

From the above disclosure of the general principles of the present invention and the preceding detailed description of at least one preferred embodiment, those skilled in the art will readily comprehend the various modifications to which this invention is susceptible. Therefore, I desire to be limited only by the scope of the following claims and equivalents thereof.

I claim:

1. A system for inspecting a work piece, the system comprising:
    an inspection platform adapted to support the work piece;
    a light source adapted to illuminate the work piece on the inspection platform;
    a camera adapted to produce an image of the work piece illuminated by the light source and positioned on the inspection platform;
    a reflective device positioned within a field of view of the camera, the reflective device including an external arcuate shaped reflective surface;
    wherein the image includes a reflected portion of the work piece which is reflected outwardly off of the reflective surface of the reflective device;
    a processing unit operably coupled to the camera to analyze the image of the work piece generated by the camera with respect to predetermined quality control standards; and
    a rejection mechanism operably coupled to the processing unit to receive a control signal from the processing unit, the rejection mechanism being operable to remove the work piece from the platform based on the control signal.

2. The system of claim 1 wherein the reflected portion is a 360° view of the work piece.

3. The system of claim 1 wherein the image includes both a direct portion that is not reflected off of the reflective device and the reflected portion.

4. The system of claim 1 wherein the reflected portion of the image is a view of a portion of the work piece that is not oriented generally orthogonal to a line of sight of the camera.

5. The system of claim 1 further comprising:
    a trigger operably coupled to the camera and positioned relative to the inspection platform to detect a position of the work piece and send a trigger signal to the camera to take an image of the work piece.

6. The system of claim 1 wherein the camera is positioned generally perpendicularly with respect to the inspection platform.

7. The system of claim 1 further comprising:
    a viewing cylinder in which the reflective device is mounted.

8. The system of claim 1 wherein the reflective device is conical.

9. The system of claim 8 wherein the conical reflective device is a truncated cone with a central aperture there through.

10. The system of claim 1 wherein the image includes an interior portion of the work piece contained within a perimeter of the work piece and the light source illuminates the interior portion.

11. The system of claim 10 wherein the interior portion is not oriented generally orthogonal to a line of sight of the camera.

12. A system for inspecting a work piece, the system comprising:
    an inspection platform adapted to support the work piece;
    a light source adapted to illuminate the work piece on the inspection platform;
    a camera adapted to produce an image of the work piece illuminated by the light source and positioned on the inspection platform;
    a reflective device positioned within a field of view of the camera;
    wherein the image includes a reflected portion of the work piece which is reflected off of the reflective device;
    a processing unit operably coupled to the camera to analyze the image of the work piece generated by the camera with respect to predetermined quality control standards;
    a rejection mechanism operably coupled to the processing unit to receive a control signal from the processing unit, the rejection mechanism being operable to remove the work piece from the platform based on the control signal; and
    an adjustable mounting mechanism coupled to the reflective device in which a distance from the reflective device to the platform is adjustable.

13. A system for inspecting a work piece, the system comprising:
    an inspection platform adapted to support the work piece;
    a light source adapted to illuminate the work piece on the inspection platform;
    a camera adapted to produce an image of the work piece illuminated by the light source and positioned on the inspection platform;
    a reflective device positioned within a field of view of the camera;
    wherein the image includes a reflected portion of the work piece which is reflected off of the reflective device;
    a processing unit operably coupled to the camera to analyze the image of the work piece generated by the camera with respect to predetermined quality control standards;
    a rejection mechanism operably coupled to the processing unit to receive a control signal from the processing unit, the rejection mechanism being operable to remove the work piece from the platform based on the control signal; and
    an adjustable mounting mechanism coupled to the camera in which a distance from the camera to the platform is adjustable.

14. A system for inspecting each of a series of serially fed work pieces in a stream of such work pieces, the system comprising:
    an inspection platform adapted to support each work piece, the platform including an inspection ramp inclined downwardly with respect to a horizontal plane and having a top end and a bottom end, each of the work pieces being serially received at the top end and discharged at the bottom end, each of the work pieces separating a distance from the adjacent work pieces and maintaining contact with an upper surface of the inspection ramp as it moves from the top end to the bottom end;

a light source adapted to illuminate each work piece on the inspection platform;

a camera adapted to produce an image of each work piece illuminated by the light source and positioned on the inspection platform;

a reflective device positioned within a field of view of the camera;

wherein the image includes a reflected portion of the work piece which is reflected off of the reflective device;

a processing unit operably coupled to the camera to analyze the image of the work piece generated by the camera with respect to predetermined quality control standards; and a rejection mechanism operably coupled to the processing unit to receive a control signal from the processing unit, the rejection mechanism being operable to remove each work piece from the platform based on the control signal.

15. The system of claim 14 wherein the upper surface of the inspection ramp is generally planar and stationary.

16. The system of claim 14 further comprising:

a feed conveyor in communication with the top end to serially feed the work pieces each of which is in contact with adjacent work pieces on the feed conveyor; and a discharge conveyor in communication with the bottom end to receive and discharge each of the work pieces at the bottom end.

17. A system for inspecting a work piece, the system comprising:

an inspection platform adapted to support the work piece;

a light source adapted to illuminate the work piece on the inspection platform;

a camera adapted to produce an image of the work piece illuminated by the light source and positioned on the inspection platform;

a reflective device positioned within a field of view of the camera;

wherein the image includes a reflected portion of the work piece which is reflected off of the reflective device;

a processing unit operably coupled to the camera to analyze the image of the work piece generated by the camera with respect to predetermined quality control standards; and a rejection mechanism operably coupled to the processing unit to receive a control signal from the processing unit, the rejection mechanism being operable to remove the work piece from the platform based on the control signal;

wherein the light source is positioned on a back side of the work piece and opposite from the camera to back light the work piece and at least a portion of the inspection platform is at least translucent to permit light from the light source to pass therethrough and illuminate the work piece.

18. A system for inspecting a work piece, the system comprising:

an inspection platform adapted to support the work piece;

a light source adapted to illuminate the work piece on the inspection platform;

a camera adapted to produce an image of the work piece illuminated by the light source and positioned on the inspection platform;

a reflective device positioned within a field of view of the camera;

wherein the image includes a reflected portion of the work piece which is reflected off of the reflective device;

a processing unit operably coupled to the camera to analyze the image of the work piece generated by the camera with respect to predetermined quality control standards; and a rejection mechanism operably coupled to the processing unit to receive a control signal from the processing unit, the rejection mechanism being operable to remove the work piece from the platform based on the control signal;

wherein the image is produced with only the single camera.

19. The system of claim 18 wherein the reflective device is non-planar.

20. A system for inspecting each of a series of serially fed work pieces in a stream of such work pieces, the system comprising:

an inspection ramp inclined downwardly with respect to a horizontal plane and having a top end and a bottom end, each of the work pieces being serially received at the top end and discharged at the bottom end, each of the work pieces separating a distance from the adjacent work pieces and maintaining contact with an upper surface of the inspection ramp as it moves from the top end to the bottom end, wherein the upper surface of the inspection ramp is generally planar and stationary;

a light source adapted to illuminate the work piece on the inspection platform;

a single camera adapted to produce an image of the work piece illuminated by the light source and positioned on the inspection platform;

wherein the camera is oriented generally perpendicularly with respect to the inspection platform;

wherein the light source is positioned on a back side of the work piece and opposite from the camera to back light the work piece and at least a portion of the inspection ramp is at least translucent to permit light from the light source to pass therethrough and illuminate the work piece;

a conical reflective device positioned within a field of view of the camera;

wherein the image includes a reflected portion of the work piece which is reflected off of the reflective device and a direct portion that is not reflected off of the reflective device;

wherein the image further includes an interior portion of the work piece contained within a perimeter of the work piece and the light source illuminates the interior portion;

an adjustable mounting mechanism coupled to the reflective device and the camera in which a first distance from the reflective device to the platform is adjustable as well as a second distance from the camera to the platform is adjustable;

a processing unit operably coupled to the camera to analyze the image of the work piece generated by the camera with respect to predetermined quality control standards;

a trigger operably coupled to the camera and positioned relative to the inspection ramp to detect a position of the work piece and send a trigger signal to the camera to take an image of the work piece; and a rejection mechanism operably coupled to the processing unit to receive a control signal from the processing unit, the rejection mechanism being operable to remove the work piece from the platform based on the control signal.

21. The system of claim 20 further comprising:
a feed conveyor in communication with the top end to serially feed the work pieces each of which is in contact with adjacent work pieces on the feed conveyor; and
a discharge conveyor in communication with the bottom end to receive and discharge each of the work pieces at the bottom end.

22. A method of inspecting a work piece, the method comprising the steps of:
positioning the work piece on an inspection platform;
illuminating the work piece on the inspection platform with a light source;
activating a camera to produce an image of the work piece illuminated by the light source;
positioning a reflective device having an external arcuate shaped reflective surface within the field of view of the camera;
reflecting at least a portion of the field of view of the camera outwardly off of the external arcuate shaped reflective surface so that the image includes the reflected portion of the work piece;
analyzing the image with respect to predetermined quality control standards; and
removing the work piece from the inspection platform in a first direction if the image thereof does not satisfy the predetermined quality control standards and in a second direction if the image does satisfy the predetermined quality control standards.

23. The method of claim 22 wherein the image includes at least an interior portion of the work piece within a perimeter of the work piece.

24. The method of claim 22 wherein the reflecting further comprises:
positioning a reflective device in the field of view of the camera, wherein a shape of the reflective device is selected from the group consisting of non-planar, arcuate and conical shapes.

25. A method of inspecting a work piece, the method comprising the steps of:
positioning the work piece on an inspection platform;
illuminating the work piece on the inspection platform with a light source, wherein the illuminating further comprises back lighting the work piece from a position generally opposite from the camera, at least a portion of the inspection platform is at least translucent to permit passage of light from the light source through the inspection platform to illuminate the work piece;
activating a camera to produce an image of the work piece illuminated by the light source;
reflecting at least a portion of the field of view of the camera so that the image includes the reflected portion of the work piece;
analyzing the image with respect to predetermined quality control standards; and
removing the work piece from the inspection platform in a first direction if the image thereof does not satisfy the predetermined quality control standards and in a second direction if the image does satisfy the predetermined quality control standards.

26. A method of inspecting each of a series of serially fed work pieces the method comprising the steps of:
positioning the work piece on an inspection platform;
wherein the positioning step further comprises feeding the work pieces to a top end of a downwardly inclined inspection ramp, wherein each of the work pieces is in contact with an adjacent work piece at the top end;
moving each of the work pieces downwardly along the inspection ramp, over the inspection platform and toward a bottom end of the inspection ramp;
generating a spacing distance on the at the inspection platform between each of the work pieces and adjacent work pieces;
illuminating the work piece on the inspection platform with a light source;
activating a camera to produce an image of the work piece illuminated by the reflecting at least a portion of the field of view of the camera so that the image includes the reflected portion of the work piece;
analyzing the image with respect to predetermined quality control standards; and
removing the work piece from the inspection platform in a first direction if the image thereof does not satisfy the predetermined quality control standards and in a second direction if the image does satisfy the predetermined quality control standards.

27. The method of claim 26 wherein the moving of the work pieces downwardly along the inspection ramp is accomplished by gravity and the inspection ramp is generally planar and stationary.

28. A method of inspecting each of a series of plastic molded caps each having a liner therein, the method comprising the steps of:
feeding the caps to a top end of a downwardly inclined inspection ramp, wherein each of the caps is in contact with an adjacent cap at the top end;
moving each of the caps downwardly along the Inspection ramp, over the inspection platform and toward a bottom end of the inspection ramp;
wherein the moving of the caps downwardly along the inspection ramp is accomplished by gravity and the inspection ramp is generally planar and stationary;
generating a spacing distance on the inspection ramp between each of the caps and adjacent caps;
illuminating the cap on the inspection ramp with a light source;
activating a camera to produce an image of the cap illuminated by the light source;
wherein the illuminating further comprises back lighting the cap from a position generally opposite from the camera, at least a portion of the inspection platform is at least translucent to permit passage of light from the light source through the inspection platform to illuminate the cap;
positioning a reflective device in the field of view of the camera, wherein a shape of the reflective device is selected from the group consisting of non-planar, arcuate and conical shapes;
reflecting at least a portion of the field of view of the camera so that the image includes the reflected portion of the cap;
wherein the image includes at least an interior portion of the cap within a perimeter of the cap;
analyzing the image with respect to predetermined quality control standards; and
removing the cap from the inspection platform in a first direction if the image thereof does not satisfy the predetermined quality control standards and in a second direction if the image does satisfy the predetermined quality control standards.

* * * * *

UNITED STATES PATENT AND TRADEMARK OFFICE
CERTIFICATE OF CORRECTION

PATENT NO. : 6,784,447 B2
DATED : August 31, 2004
INVENTOR(S) : Joseph P. Gochar, Jr.

It is certified that error appears in the above-identified patent and that said Letters Patent is hereby corrected as shown below:

<u>Column 14,</u>
Lines 12-14, "illuminated by the reflecting at least" should read
-- illuminated by the light source;

reflecting at least --.
Line 32, "Inspection" should read -- inspection --.

Signed and Sealed this

Twenty-sixth Day of April, 2005

JON W. DUDAS
*Director of the United States Patent and Trademark Office*